US007078209B2

(12) United States Patent
Ledford et al.

(10) Patent No.: US 7,078,209 B2
(45) Date of Patent: Jul. 18, 2006

(54) CAK INHIBITORS AND USES THEREOF

(75) Inventors: Brian Ledford, Attleboro, MA (US); Cameron Stuver Moody, Lexington, MA (US); Michael Mullican, Needham, MA (US); Mark Namchuk, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 221 days.

(21) Appl. No.: 10/166,234

(22) Filed: Jun. 6, 2002

(65) Prior Publication Data

US 2003/0119793 A1 Jun. 26, 2003

Related U.S. Application Data

(60) Provisional application No. 60/296,239, filed on Jun. 6, 2001.

(51) Int. Cl.
*C12N 9/12* (2006.01)
*C07G 17/00* (2006.01)
*A61K 31/444* (2006.01)

(52) U.S. Cl. ...................... 435/194; 435/267; 514/279; 514/283

(58) Field of Classification Search ................ 435/194, 435/264, 267; 514/222.8, 277, 279, 283

See application file for complete search history.

(56) References Cited

U.S. PATENT DOCUMENTS 5,091,537 A 2/1992 Fischer et al.
5,705,350 A * 1/1998 Mudryj et al. ............. 435/7.21

FOREIGN PATENT DOCUMENTS

EP 0 404 190 A 12/1990

OTHER PUBLICATIONS

Pauls, H., et al., "Umsetzungen mit CH-aciden Verbindungen and Übergang in Indolizine," *Chemische Berichten*, 10:1294-1303 (1997).

Mezentseva, M.V., et al., "Synthesis and Antitumor Activity of Pyrrolo [3,2-d] Pyrimidines," *Pharmaceutical Chemistry Journal*, 25:858-864 (1991).

Sato, K., et al., "Studies of heterocyclic compound. XI. The synthesis of oxazolo [3,2-b] pyridazinium perchlorates and their reactions with some C-nucleophiles", *Chemical abstract*, 87(13), abstract No. 102255a, (1977).

Abd el Salam, O., "Synthesis of some new pyrimido [5,4-a] indolizines," *Monatshefte für Chemie*, 131:959-965 (Sep. 2000).

* cited by examiner

*Primary Examiner*—Jean C. Witz
*Assistant Examiner*—Susan Hanley
(74) *Attorney, Agent, or Firm*—Karen E. Brown; Vertex Pharmaceuticals Incorporated

(57) ABSTRACT

The present invention relates to compounds useful as inhibitors of CAK, compositions thereof. The present invention also relates to methods using the compositions for treating CAK-mediated diseases, such as fungal infections.

22 Claims, No Drawings

CAK INHIBITORS AND USES THEREOF

CROSS-REFERENCE TO RELATED APPLICATIONS

The present invention claims the benefit of U.S. Provisional Application No. 60/296,239, filed Jun. 6, 2001.

TECHNICAL FIELD OF THE INVENTION

The present invention relates to methods of inhibiting CAK, compounds useful as inhibitors of CAK, and compositions thereof. The present invention also relates to methods using the compounds and compositions for treating CAK-mediated diseases, such as fungal infections.

BACKGROUND OF THE INVENTION

There is an increasing recognition that the medical significance of fungal infections has dramatically increased. There is a rising incidence of these infections as well as recognition that fungal species heretofore thought to be non-pathogenic are indeed a cause of disease. Presently, there are limited therapeutic options for the treatment of these infections and there is an urgent need for the development of additional effective and safe antifungal agents.

Human infections caused by fungi can be divided into four main groups depending on the location of the infection. These include 1) superficial infections of the outer layers of the skin, nails, and hair follicles and are usually caused by Dermatophytes and Candida species, 2) subcutaneous infections of deeper layers of the skin and subcutaneous tissues and are caused most commonly by Sporothrix schenckii and Pseudallescheria boydii, 3) mucosal infections of the gastrointestinal tract and the genitourinary tract and are usually caused by Candia species, and 4) systemic infections of the bloodstream and deep organs of the body which are caused by by an increasing number of fungal pathogens.

Systemic fungal infections, in particular, have become a significant medical problem. According to statistics from the Centers for Disease Control and Prevention, the incidence of systemic fungal infections, particularly those caused by Candida species have climbed dramatically over the last 20 years. Candida species are the fourth most common microorganisms isolated from the bloodstream of hospitalized patients in the United States. These infections are serious: despite antifungal therapy, the attributable mortality of Candida species bloodstream infections is 30–40%.

The majority of systemic fungal infections are caused by Candida albicans. Infections by non-albicans species such as Candida glabrata, Candida tropicalis, and Candida krusei have been increasing. Though rare, infections by Aspergillus species, Mucorales, and Fusarium have also been increasing. Predisposing factors that lead to these infections includes treatment with broad-spectrum antibacterial antibiotics, a compromised immune system caused by cancer chemotherapy, treatment for transplant rejection or treatment of autoimmune illnesses with corticosteroids, and underlying illnesses such as HIV infection. Additionally elderly and debilitated persons are at risk for these infections.

The diagnosis of fungal infections is often difficult. Many opportunistic fungal infections cannot be diagnosed by routine blood or tissue culture and must be treated empirically in severely immune-compromised patients (Walsh et al. (199 1) Rev. Infect. Dis. 13:496).

At present, there is a limited number of therapeutics available to treat these infections. Therapy is further complicated by the fact that the available therapeutic agents are associated with severe toxicity and the need for intravenous access. The polyene antifungal agent, amphotericin B, has served as the cornerstone of therapy for the several decades. It is administered intravenously and is associated with fever and chills during its administration, renal insufficiency and anemia. Recently, newer lipid formulations of amphotericin B have become available and are associated with a lesser incidence of adverse effects. Azole antifungal agents are the othermajor class of antifungal therapeutics that are available for the treatment of fungal infections. Unlike amphotericin B, these agents are administered both intravenously and orally. In general, these agents are not considered as potent as amphotericin B and are usually used in less severe infections. They have also been associated with hepatic dysfunction. Another recent problem that has been noted is the increasing incidence of resistance to the azole antifungal agents.

The development of effective and safe treatment of fungal infections has lagged behind the therapy for bacterial infections. There are numerous commentators who have speculated on this apparent neglect. See, for example, Georgopapadakou et al. (1994) Science 264:371. First, it is difficult. Like mammalian cells, fungi are eukaryotes and thus agents that inhibit fungal protein, RNA, or DNA biosynthesis may do the same in the patient's own cells, producing toxic side effects and the attendant difficulty administering this agent to a patient. Second, life-threatening fungal infections were thought, until recently, to be too infrequent to warrant aggressive research by the pharmaceutical industry. Finally, because pathogenic fungi are difficult to culture, and because many of them do not reproduce sexually, microbiological and genetic research into the disease-causing organisms has lagged far behind research into other organisms.

The progression of a proliferating eukaryotic cell through the cell-cycle checkpoints is controlled by an array of regulatory proteins that guarantee that mitosis occurs at the appropriate time. Protein phosphorylation is the most common post-translational modification that regulates processes inside the cells, and a large number of cell cycle transitions are regulated by, in addition to protein-protein interactions, the phosphorylation states of various proteins. In particular, the execution of various stages of the cell-cycle is generally believed to be under the control of a large number of mutually antagonistic kinases and phosphatases.

A paradigm for these controls is the CDC2 protein kinase, a cyclin-dependent kinase (CDK) whose activity is required for the triggering of mitosis in eukaryotic cells (for reviews, see Hunt (1989) Curr. Opin. Cell Biol. 1:268–274; Lewin (1990) Cell 61:743–752; and Nurse (1990) Nature 344: 503–508). During mitosis, the CDC2 kinase appears to trigger a cascade of downstream mitotic phenomena such as metaphase alignment of chromosomes. segregation of sister chromatids in anaphase, and cleavage furrow formation. Many target proteins involved in mitotic entry of the proliferating cell are directly phosphorylated by the CDC2 kinase. For instance, the CDC2 protein kinase acts by phosphorylating a wide variety of mitotic substrates involved in regulating the cytoskeleton of cells, such that entry into mitosis is coordinated with dramatic rearrangement of cytoskeletal elements.

The CDC2 kinase is subject to multiple levels of control. One well-characterized mechanism regulating the activity of CDC2 involves the phosphorylation of tyrosine, threonine and serine residues, the phosphorylation level of which varies during the cell-cycle (Krekk et al. (1991) EMBO J. 10:305–316; Draetta et al. (1988) Nature 336:738–744;

Dunphy et al. (1989) Cell 58:181–191; Morla et al. (1989) Cell 58:193–20–3); Gould et al. (1989) Nature 342:39–45; and Solomon et al. (1990) Cell 63:1013–1024).

The phosphorylation of CDC2 on Tyr-15 and Thr-14, two residues located in the putative ATP binding site of the kinase, negatively regulates kinase activity. This inhibitory phosphorylation of CDC2 is mediated at least in part by the weel and mikI tyrosine kinases (Russel et al. (1987) Cell 49:559–567; Lundgren et al. (1991) Cell 64:1111–1122; Featherstone et al. (1991) Nature 349:808–811; and Parker et al. (1992) PNAS 89:2917–2921). These kinases act as mitotic inhibitors, over-expression of which causes cells to arrest in the G2 phase of the cell-cycle. By contrast, loss of function of weel causes a modest advancement of mitosis, whereas loss of both weel and mikI function causes grossly premature mitosis,. uncoupled from all checkpoints that normally restrain cell division (Lundgren et al. (199 1) Cell 64:1111–1122).

As the cell is about to reach the end of G2, dephosphorylation of the CDC2- inactivating Thr-14 and Tyr-15 residues occurs leading to activation of the CDC2 complex as a kinase. A stimulatory phosphatase, known as CDC25, is responsible for Tyr-15 and Thr-14 dephosphorylation and serves as a rate-limiting mitotic activator. (Dunphy et al. (1991) Cell 67:189–196, Lee et al. (1992) Mol. Biol. Cell. 3:73–84; Millar et al. (1991) EMBO J :4301–4309; and Russell et al. (1986) Cell 45:145–153).

Recent evidence indicates that both the CDC25 phosphatase and the CDC2-specific tyrosine kinases are detectably active during interphase, suggesting that there is an ongoing competition between these two activities prior to mitosis (Kumagai et al. (1992) Cell 70:139–151; Smythe et al. (1992) Cell 68:787–797; and Solomon et al. (1990) Cell 63:1013–1024). This situation implies that the initial decision to enter mitosis involves a modulation of the equilibrium of the phosphorylation state of CDC2 at these residues, which is likely controlled by variation of the rate of tyrosine dephosphorylation of CDC2 and/or a decrease in the rate of its tyrosine phosphorylation.

In addition to the inhibitory phosphorylation of Cdks, most Cdks also require binding of a cyclin and phosphorylation of a threonine (residue 169 in *S cerevisiae* p34cdc2). This phosphorylation is carried out by CAK, the"Cdk-activating kinase". The *cerevisiae* CAKI binds tightly to and phosphorylates Cdc28, thereby allowing its subsequent activation by the binding of a cyclin. The CAKI gene is essential for yeast cell viability, and Cdc28 phosphorylation and activity are conditionally inhibited in a CAKI temperature-sensitive mutant. For instance, CAKI is required for vegetative growth and spore wall morphogenesis (see Wagner et al. (1997) EMBO J. 16:1305; and Kaldis (1999) Cell Mol Life Sci 55:284).

In vertebrates, CAK is a trimeric enzyme containing CDK7, cyclin H, and MATI. CAK from the budding yeast was identified as an unusual 44-kilodalton protein kinase, CAKI, that is only distantly related to CDKs. CAKI accounted for most CAK activity in yeast cell lysates, and its activity was constant throughout the cell cycle. The CAK I gene was essential for cell viability. Thus, the major CAK in *S. cerevisiae* is distinct from the vertebrate enzyme, suggesting that budding yeast and vertebrates may have evolved different mechanisms of CDK activation.

Apart from phosphorylation, the regulation of the Cdc2-cyclin B complex involves a small ancillary subunit called p9sucl, a member of the Sucl/Cks family of proteins. Although p9 is not required for the catalytic activity of Cdc2, it appears to be responsible for the interaction of MPF with some of its critical regulators. For example, Xenopus egg extracts from which p9 has been completely removed by immunodepletion cannot undergo cell-cycle transitions normally. Specifically, mitotic egg extracts lacking p9 cannot exit mitosis properly due to a defect in the ubiquitin-mediated proteolysis of cyclin B. A molecular description of how p9 helps to mediate the exit from mitosis should provide valuable insights into Cdk regulation.

In the past decade, however, more antifungal drugs have become available. Nevertheless there are still major weaknesses in their spectra, potency, safety, and pharmacokinetic properties, and accordingly it is desirable to improve the panel of anti-fungal agents available to the practitioner.

SUMMARY OF THE INVENTION

The present invention provides a method of inhibiting CAK comprising the step of contacting said CAK with a compound of formula I:

(I)

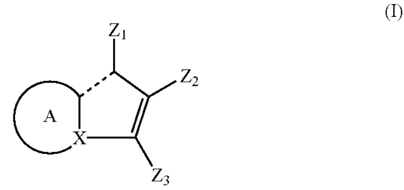

wherein:

X is N or =C;

Y is =C when X is N;

Y is N when X is =C;

ring A, taken together with X, is a 5–7 membered monocyclic carbocyclic or heterocyclic aromatic or non-aromatic ring;

wherein ring A has up to 3 substituents independently selected from halogen, —OH, —$NO_2$, —$CF_3$, —$OCF_3$, R, —OR, —O-benzyl, —O-phenyl, 1,2-methylenedioxy, —$NR_2$, —COR, —$CO_2$R, —CON(R)$_2$, —NRCON(R)$_2$, —NRCOR, —$NRCO_2$R, —CO—COR, —CONRN(R)$_2$, —$SO_2$R, —SOR, —SON(R)$_2$, —$SO_2$N(R)$_2$ and —$NRSO_2$R;

wherein each R is independently H, (C1–C6) straight or branched alkyl, (C2–C6) straight or branched alkenyl or alkynyl;

one of $Z^1$ and $Z^3$ is selected from —CN, —$N_3$, acetenyl or cyclopropyl, and the other of $Z^1$ and $Z^3$ is:

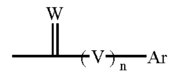

wherein:

n is 0 or 1;

W is O or S;

V is —NH—;

Ar is a 5–10 membered monocyclic or bicyclic aromatic carbocyclic or aromatic heterocyclic ring;

wherein Ar has up to 3 substituents selected from halogen, —OH, —$NO_2$, —$CF_3$, —$OCF_3$ R, —OR, —O-benzyl, —O-phenyl, 1,2-methylenedioxy, —$NR_2$, —COR, —$CO_2$R, —CON(R)$_2$, —NRCON(R)$_2$, —NRCOR, —$NRCO_2$R, —CO—COR, —CONRN(R)$_2$, —$SO_2$R, —SOR, —SON(R)$_2$, —$SO_2$N(R)$_2$ and —$NRSO_2$R;

wherein each R is independently as defined above;

$Z^2$ is $NHR^1$;

wherein $R^1$ is H or C1–C6 straight or branched alkyl.

The present invention also provides compounds useful in inhibiting CAK, and compositions comprising said compound and a pharmaceutically acceptable carrier.

The present invention also provides methods of treating CAK-mediated diseases and fungal infections.

DETAILED DESCRIPTION OF THE INVENTION

Definitions

The following definitions are employed in the below description.

The term"heterocyclic ring" as used herein means rings containing up to 4 heteroatoms in the ring independently selected from N, NH, O, S, SO or $SO_2$, Aromatic heterocyclic rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyli 2-thienyl, or 3-thienyl.

Non-aromatic heterocyclic rings includes 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxane, benzotriazol-1-yl, benzopyrrolidine, benzopiperidine, benzoxolane, benzothiolane, benzothiane. Non-aromatic heterocyclic rings, such as those above, may be optionally fused with an aromatic carbocyclic or aromatic carbocyclic ring.

The present invention provides a method of inhibiting CAK comprising the step of contacting said CAK with a compound of formula I:

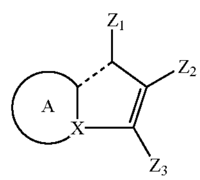

wherein:

X is N or =C;

Y is =C when X is N;

Y is N when X is =C;

ring A, taken together with X, is a 5–10 membered monocyclic or bicyclic carbocyclic or heterocyclic aromatic or non-aromatic ring;

wherein ring A has up to 3 substituents independently selected from halogen, —OH, —$NO_2$, —$CF_3$, —$OCF_3$, R, —OR, —O-benzyl, —O-phenyl, 1,2-methylenedioxy, —$NR_2$, —COR, —$CO_2$R, —CON(R)$_2$, —NRCON(R)$_2$, —NRCOR, —$NRCO_2$R, —CO—COR, —CONRN(R)$_2$, —$SO_2$R, —SOR, —SON(R)$_2$, —$SO_2$N(R)$_2$ and —$NRSO_2$R;

wherein each R is independently H, ($C_1$–C6) straight or branched alkyl, (C2–C6) straight or branched alkenyl or alkynyl;

one of $Z^1$ and $Z^3$ is selected from —CN, —$N_3$, acetenyl or cyclopropyl, and the other of $Z^1$ and $Z^3$ is:

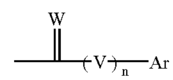

wherein:

n is 0 or 1;

W is O or S;

V is —NH—;

Ar is a 5–10 membered monocyclic or bicyclic aromatic carbocyclic or aromatic heterocyclic ring;

wherein Ar has up to 3 substituents selected from halogen, —OH, —$NO_2$, —$CF_3$, —$OCF_3$, R, —OR, —O-benzyl, —O-phenyl, 1,2-methylenedioxy, —$NR_2$, —COR, —$CO_2$R, —CON(R)$_2$, —NRCON(R)$_2$, —NRCOR, —$NRCO_2$R, —CO—COR, —CONRN(R)$_2$, —$SO_2$R, —SOR, —SON(R)$_2$, —$SO_2$N(R)$_2$ and —$NRSO_2$R;

wherein each R is independently as defined above;

$Z^2$ is $NHR^1$;

wherein $R^1$ is H or C1–C6 straight or branched alkyl.

According to another embodiment of said method, ring A is a 5- or 6-membered carbocyclic ring. According to another embodiment, ring A is phenyl. According to yet another embodiment, ring A is cyclopentyl or cyclohexyl.

According to another embodiment of said method, ring A is a 5- or 6-membered heterocyclic ring.

According to another embodiment of said method, ring A is a 5- or 6-membered aromatic heterocyclic ring selected from phenyl, 2-furyl, 3-furyl, 2-thienyl, 3-thienyl, 2-pyridyl, 3-pyridyl, 4-pyridyl, pyrrolyl, oxazolyl, thiazolyl, imidazolyl,pyrazolyl, 2-pyrazolinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl or 1,3,5-trithianyl. More preferably, ring A is phenyl, 2-furyl, 3-furyl, 2-thienyl, 3-thienyl, 2-pyridyl, 3-pyridyl or 4-pyridyl. Preferably, ring A is phenyl.

According to yet another embodiment of said method, ring A is a 5- or 6-membered non-aromatic heterocyclic ring.

According to another embodiment of said method, ring A is selected from 5- or 6-membered rings containing up to 4 heteroatoms or heteroatom groups in the ring selected from O, N, NH, S, SO or $SO_2$. According to another embodiment of said method, X is N and Y is =C.

According to another embodiment of said method, X is =C and Y is N.

According to another embodiment, $Z_1$ is —CN, —$N_3$, acetenyl or cyclopropyl. According to yet another embodiment, $Z_1$ is —CN or —$N_3$. According to yet another embodiment, $Z_1$ is —CN.

According to another embodiment of said method, $Z_2$ is —N($R^1$)$_2$, wherein the first $R^1$ is H, and the second $R^1$ is C1–C6 alklyl.

According to yet another embodiment of said method, $Z_2$ is —$NH_2$.

According to another embodiment of said method, $Z_3$ is:

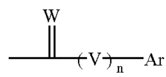

wherein W, V, n, and Ar are as defined above.

According to another embodiment of $Z_3$:

W is O;

n is 0;

Ar is as defined above.

According to another embodiment of said method, Ar is selected from phenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl or 1,3,5-trithianyl, wherein Ar has up to three substituents, as defined above.

According to yet another embodiment of said method, Ar is phenyl, 2-furyl, 3-furyl, 2-thienyl, 3-thienyl, 2-pyridyl, 3-pyridyl, 4-pyridyl, pyrrolyl, oxazolyl, thiazolyl or imidazolyl, wherein Ar has up to three substituents, as defined above.

According to yet another embodiment of said method, Ar is phenyl, 2-pyridyl, 3-pyridyl or 4-pyridyl, wherein Ar has up to three substituents, as defined above.

According to yet another embodiment of said method, Ar is phenyl containing up to three substituents, as defined above.

According to another embodiment of said method, Ar has up to three substituents independently selected from halogen, —OH, —$NO_2$, —$CF_3$, —$OCF_3$, R, —OR, —$NR_2$, —COR, —$CO_2R$, —$CON(R)_2$, —$SO_2R$, —SOR, —$SON(R)_2$, —$SO_2N(R)_2$ and —$NRSO_2R$;

wherein each R is independently as defined above.

According to another embodiment of said method, Ar has up to three substituents independently selected from halogen, —OH, —$NO_2$, —$CF_3$, —$OCF_3$, R, —OR, or —$NR_2$;

wherein each R is independently as defined above.

According to another embodiment of said method, Ar has up to two substituents, wherein said substituents are as defined above.

According to another embodiment of said method, Ar has one substituent, wherein said substituent is as defined above.

According to another embodiment, the present invention provides a method of inhibiting CAK enzyme, comprising the step of contacting said CAK with a compound of formula I':

(I')5

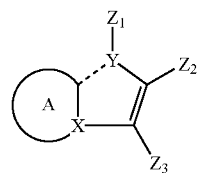

wherein:

X is N or =C;

Y is =C when X is N;

Y is N when X is =C;

ring A, taken together with X, is a 5–7 membered monocyclic or bicyclic carbocyclic or heterocyclic aromatic or non-aromatic ring;

wherein ring A has up to 3 substituents independently selected from halogen, —OH, —$NO_2$, —$CF_3$, —$OCF_3$, R, —OR, —O-benzyl, —O-phenyl, 1,2-methylenedioxy, —$NR_2$, —COR, —$CO_2R$, —$CON(R)_2$, —$NRCON(R)_2$, —NRCOR, —$NRCO_2R$, —CO—COR, —$CONRN(R)_2$, —$SO_2R$, —SOR, —$SON(R)_2$, —$SO_2N(R)_2$ and —$NRSO_2R$;

wherein each R is independently H, (C1–C6) straight or branched alkyl, (C2–C6) straight or branched alkenyl or alkynyl;

one of $Z^1$ and $Z^3$ is selected from —CN, —$N_3$, acetenyl or cyclopropyl, and the other of $Z^1$ and $Z^3$ is:

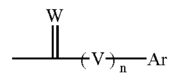

wherein:

n is 0 or 1;

W is O or S;

V is —NH—;

Ar is a 5–10 membered monocyclic or bicyclic aromatic carbocyclic or aromatic heterocyclic ring;

wherein Ar has up to 3 substituents selected from halogen, —OH, —$NO_2$, —$CF_3$, —$OCF_3$, R, —OR, —O-benzyl, —O-phenyl, 1,2-methylenedioxy, —$NR_2$, —COR, —$CO_2R$, —$CON(R)_2$, —$NRCON(R)_2$, —NRCOR, —$NRCO_2R$, —CO—COR, —$CONRN(R)_2$, —$SO_2R$, —SOR, —$SON(R)_2$, —$SO_2N(R)_2$ and —$NRSO_2R$;

wherein each R is independently as defined above;

$Z^2$ is $NHR^1$;

wherein $R^1$ is H or C1–C6 straight or branched alkyl; provided that when X is N, Y is =C, $Z^1$ is CN, $Z^2$ is —$NH_2$, W is O, and ring A, together with X is selected from:

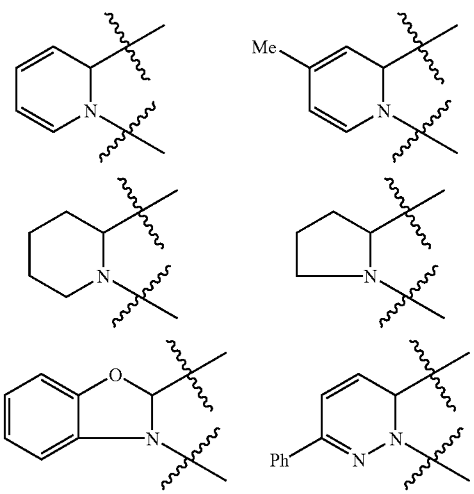

-continued

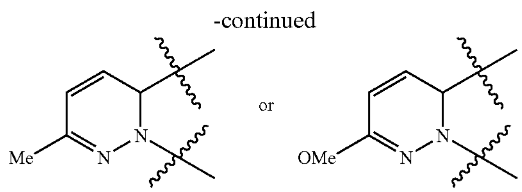

then, n is 0, and Ar is not unsubstituted phenyl.

According to another embodiment of formula (I'), ring A is a 5- or 6-membered carbocyclic ring. According to another embodiment, ring A is phenyl. According to yet another embodiment, ring A is cyclopentyl or cyclohexyl.

According to another embodiment of formula (I'), ring A is a 5- or 6-membered heterocyclic ring.

According to another embodiment of formula (I'), ring A is a 5- or 6-membered aromatic heterocyclic ring selected from phenyl, 2-furyl, 3-furyl, 2-thienyl, 3-thienyl, 2-pyridyl, 3-pyridyl, 4-pyridyl, pyrrolyl, oxazolyl, thiazolyl, imidazolyl,pyrazolyl, 2-pyrazolinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl or 1,3,5-trithianyl. More preferably, ring A is phenyl, 2-furyl, 3-furyl, 2-thienyl, 3-thienyl, 2-pyridyl, 3-pyridyl or 4-pyridyl. Preferably, ring A is phenyl.

According to yet another embodiment of formula (I'), ring A is a 5- or 6-membered non-aromatic heterocyclic ring.

According to another embodiment of formula (I'), ring A is selected from 5- or 6-membered rings containing up to 4 heteroatoms or heteroatom groups in the ring selected from O, N, NH, S, SO or $SO_2O$.

According to another embodiment of formula (I'), X is N and Y is =C.

According to another embodiment of formula (I'), X is =C and Y is N.

According to another embodiment of formula (I'), $Z_1$ is —CN, —$N_3$, acetenyl or cyclopropyl. According to yet another embodiment, $Z_1$ is —CN or —$N_3$. According to yet another embodiment, $Z_1$ is —CN.

According to another embodiment of formula (I'), $Z_2$ is —$N(R^1)_2$, wherein the first $R^1$ is H, and the second $R^1$ is C1–C6 alklyl.

According to yet another embodiment of formula (I'), $Z_2$ is —$NH_2$.

According to another embodiment of formula (I'), $Z_3$ is:

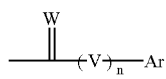

wherein W, V, n, and Ar are as defined above.

According to another embodiment of Z3:

W is O;

n is 0;

Ar is as defined above.

According to another embodiment of formula (I'), Ar is selected from phenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl or 1,3,5-trithianyl, wherein Ar has up to three substituents, as defined above.

According to yet another embodiment of formula (I'), Ar is phenyl, 2-furyl, 3-furyl, 2-thienyl, 3-thienyl, 2-pyridyl, 3-pyridyl, 4-pyridyl, pyrrolyl, oxazolyl, thiazolyl or imidazolyl, wherein Ar has up to three substituents, as defined above.

According to yet another embodiment of formula (I'), Ar is phenyl, 2-pyridyl, 3-pyridyl or 4-pyridyl, wherein Ar has up to three substituents, as defined above.

According to yet another embodiment of formula (I'), Ar is phenyl containing up to three substituents, as defined above.

According to another embodiment of formula (I'), Ar has up to three substituents independently selected from halogen, OH, —$NO_2$, —$CF_3$, —$OCF_3$, R, —OR, —$NR_2$, —COR, —$CO_2R$, —$CON(R)_2$, —$SO_2R$, —SOR, —$SON(R)_2$, —$SO_2N(R)_2$ and —$NRSO_2R$;

wherein each R is independently as defined above.

According to another embodiment of formula (I'), Ar has up to three substituents independently selected from halogen, —OH, —$NO_2$, —$CF_3$, —$OCF_3$, R, —OR, or —$NR_2$;

wherein each R is independently as defined above.

According to another embodiment of formula (I'), Ar has up to two substituents, wherein said substituents are as defined above.

According to another embodiment of formula (I'), Ar has one substituent, wherein said substituent is as defined above.

According to another embodiment, the present invention provides methods of inhibiting CAK enzyme comprising the step of contacting said CAK with compounds of formula (II):

(II)

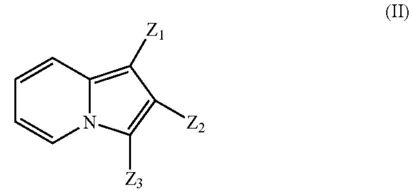

wherein:

$Z_1$ is —CN, —$N_3$, acetenyl or cyclopropyl;

$Z_2$ is —$N(R^1)_2$, wherein each $R^1$ is independently H, C1–C6 alkyl, C2–C6 alkenyl or alkynyl, wherein a —$CH_2$— in said alkyl, alkenyl or alkynyl may be replaced by —C(O)—, —C(O)—O—, —O—C(O)—, —C(O)—NH—, —NH—C(O)—, —O—, or —S—;

$Z_3$ is:

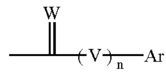

wherein W, V, Ar, m, and n are as defined above; provided that when Y is =C, $Z^1$ is CN, $Z^2$ is —$NH_2$ and W is O, then:

n is 0 and Ar is not unsubstituted phenyl.

According to another embodiment of formula (II):

W is O;

n is 0;

Ar is phenyl or a 5- or 6-membered aromatic heterocyclic ring;

wherein Ar has up to 3 substituents selected from halogen, hydroxyl, nitro, trifluoromethyl, trifluoromethoxy, (C1–C6)-straight or branched alkyl, (C2–C6)-straight or branched alkenyl, O—(C1–C4)-straight or branched alkyl, O—(C2–C4)- straight or branched alkenyl, O-benzyl, O-phenyl, 1,2-methylenedioxy, amino, carboxyl, N—[(C1–C5)-straight or branched alkyl or (C2–C5)-straight or branched alkenyl]carboxamide, N,N-di-[(C1–C5)-straight or branched alkyl or (C2–C5)-straight or branched alkenyl] carboxamide.

Other embodiments of $Z_1$, $Z_2$ and $Z_3$ in formula (II) are as recited above in the various embodiments of formula (I').

According to another embodiment, the present invention provides compounds of formula (I'), wherein said formula (I') is as defined above.

According to another embodiment, the present invention provides compounds of formula (II), wherein said formula (II) is as defined above.

Table 1 below lists some specific compounds of the present invention:

TABLE 1

| Compd. No. | Structure |
|---|---|
| 1 | 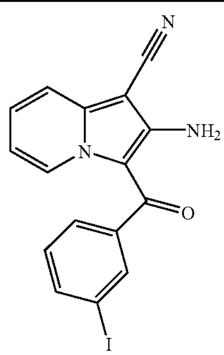 |
| 2 | 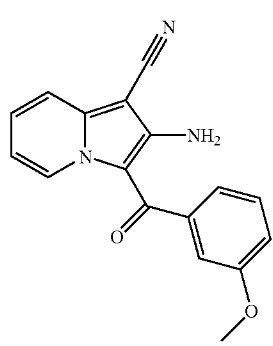 |
| 3 | 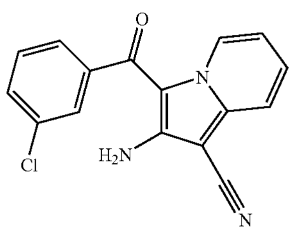 |

TABLE 1-continued

| Compd. No. | Structure |
|---|---|
| 4 | 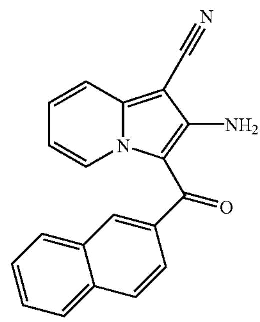 |
| 5 | 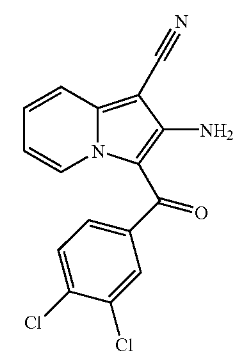 |
| 6 | 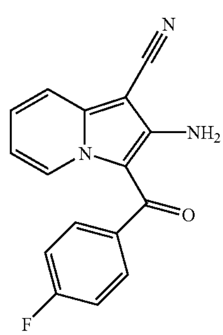 |
| 7 | 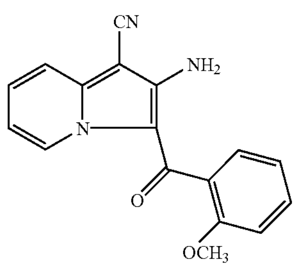 |

TABLE 1-continued

| Compd. No. | Structure |
|---|---|
| 8 | 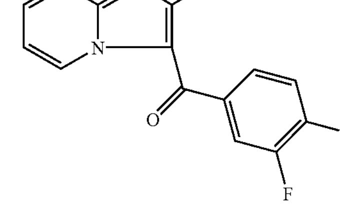 |
| 9 | 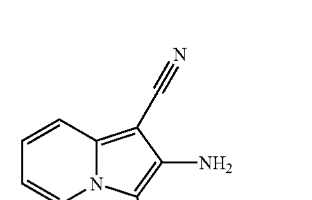 |
| 10 | 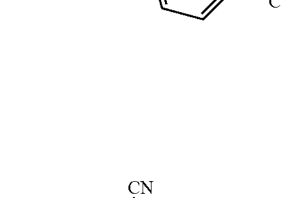 |
| 11 | 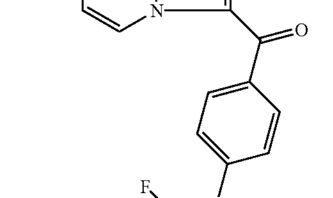 |

TABLE 1-continued

| Compd. No. | Structure |
|---|---|
| 12 | 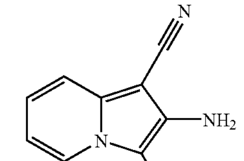 |
| 13 | 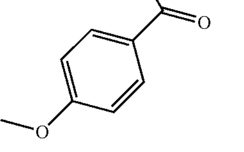 |

The compounds within the scope of the present invention can be readily prepared by methods well known in the art. Two exemplary methods of synthesizing the compounds of the present invention are illustrated below. Although the exemplary methods below are illustrate the synthesis of two specific embodiments, one of skill in the art will readily appreciate that these exemplary methods, or analogues thereof, can be readily utilized for all the compounds within the scope of the present invention.

Scheme I

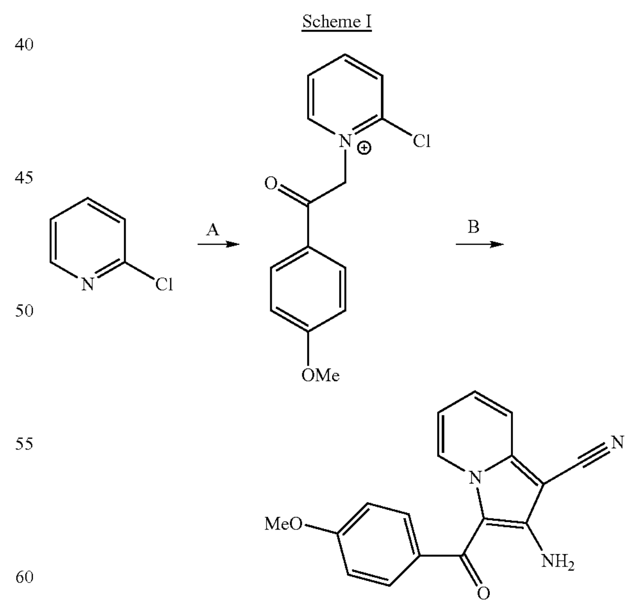

Conditions:

A: 2'-bromo-4-methoxyacetophenone, acetone;
B: malenonitrile, triethylamine, isopropanol.

Scheme II

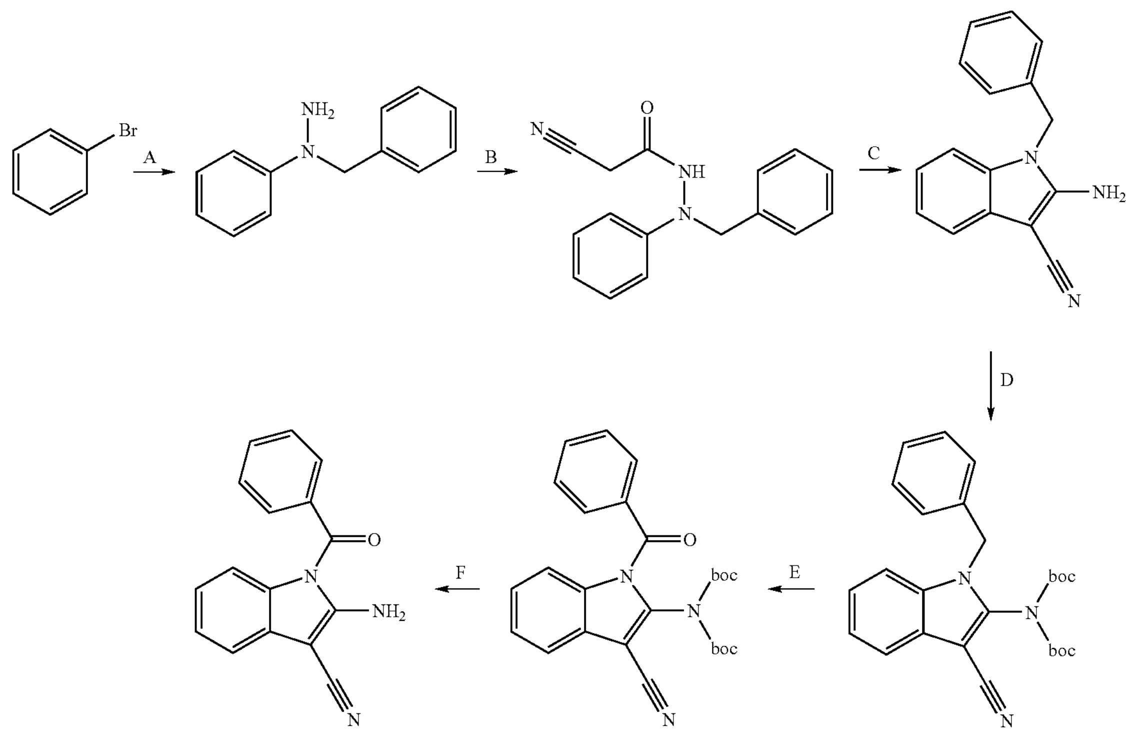

Conditions:

A: Mg, diazomethane;

B: 2-cyanoacetic acid, isopropanol;

C: $POCl_3$, dioxane;

D: di-tert-butylpyrocarbonate, $K_2CO_3$;

E: $H_2$, Pd/C, benzoyl chloride, triethylamine;

F: trifluoroacetic acid.

According to another embodiment, this invention provides compositions comprising a compound of formula (I) and a pharmaceutically acceptable carrier.

According to another embodiment, this invention provides compositions comprising a compound of formula (I') and a pharmaceutically acceptable carrier.

According to another embodiment, this invention provides compositions comprising a compound of formula (II) and a pharmaceutically acceptable carrier.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxy methylcellulose, polyacrylates, waxes, polyethylene-polyoxypropylene-block polymers, polyethylene glycol and wool fat.

As used herein, the described compounds used in the pharmaceutical compositions and methods of this invention, are defined to include pharmaceutically acceptable derivatives thereof. A"pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote repair or prevent damage of neurons from disease or physical trauma.

If pharmaceutically acceptable salts of the described compounds are used, those salts are preferably derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The described compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compositions of the present invention may be administered orally, parenterally, by inhalation spray, topically, rectally, nasally, buccally, vaginally or via an implanted reservoir. The term"parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of a described compound that may be combined with the carrier materials to produce a single dosage form will vary depending upon the host treated and the particular mode of administration. Preferably, the compositions should be formulated so that a dosage of between 0.01–100 mg/kg body weight/day of the described compound can be administered. patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

According to another embodiment, the compounds of the present invention are useful in methods for treating diseases mediated by CAK.

The compounds of the present invention can be used in the treatment of Candidiasis, an opportunistic infection that commonly occurs in debilitated and immuno-compromised patients. Such infections are observed in patients with leukemias and lymphomas, in people who are receiving immunosuppressive therapy, and in patients with such predisposing factors as diabetes mellitus or AIDS. where fungal infections are a particular problem.

According to another embodiment, the compounds of the present invention can be used in methods for treating mycotic infections caused by, for example, *Candida albicans, Candida stellatoidea, Candida tropicalis, Candida parapsilosis, Candida krusei, Candida pseudotropicalis, Candida guilliermondii, Candida glabrata, Candida lusitaniae, Candida rugosa*, or *Candida dubliniensis.*

According to another embodiment, the compounds of the present invention are also useful as additives in feed for livestock to promote weight gain. Thus, the present invention provides a method of promoting weight gain in livestock, comprising the step of administering to said livestock a food additive comprising a composition comprising a compound according to the present invention.

According to another embodiment, the compounds of the present invention are useful in agriculture for treating fungal infection in plants. Thus, the present invention provides a method of treating or preventing fungal infection in a plant, comprising the step of administering to the plant a composition comprising a compound according to the present invention.

According to another embodiment, the present invention provides disinfectant formulations comprising a compound according to the present invention. Thus, the present invention provides a method of removing or preventing fungal contamination in an inanimate surface, comprising the step of contacting the inanimate surface with a composition comprising a compound according to the present invention.

In order that this invention be more fully understood, the following examples are set forth. These examples are for the purpose of illustration only and are not to be construed as limiting the scope of the invention in any way.

EXAMPLE 1

Activity of CDK activating kinase (CAK) from *Candida albicans* was measured by following the phosphorylation of human cyclin dependent kinase 2 (CDK 2) with $^{33}$P labeled ATP. Reactions were carried out at room temperature in 100 mM HEPES, pH 7.5, 1 mM $MgCl_2$, 100 mM NaCl and 1 mM DTT. Final concentrations of CAK and CDK2 were 2 nM and 300 nM, respectively. The CDK-2 substrate was inactivated with 5' fluorosulfonylbenzoyladenosine (FSBA) to oblate its intrinsic ATPase activity. Test compounds in DMSO (final concentrations 30 μM, 1.5% DMSO) were first incubated with CAK and CDK2 for 40 minutes, then the reaction initiated by addition of $^{33}$P ATP (final concentration 10 μM, specific activity=0.6 Ci/mmol, NEN, Boston, Mass.). The reaction was allowed to proceed for 40 minutes and quenched by addition of 10% TCA containing 250 mM ATP. The quenched reaction was harvested onto GF/C glass fiber filter plates (Packard, Meriden, Conn.) using a Tomtec 9600 cell harvester (Tomtec, Hamden, Conn.), washed with 5% TCA and water. The plates were then treated with 50 μl of scintillation fluid and counted using a Packard top count (Packard, Meriden, Conn.). $K_i$ values for inhibitory compounds were determined using the same assay at a series of compound concentrations.

Assay Conditions:

100 mM HEPES, pH 7.5

1 mM MgCl2

100 mM NaCl 1 mM DTT 2 nM CAK 0.3 μM CDK2·FSBA 1.5% DMSO (compounds are dissolved in DMSO)

10 μM ATP (specific activity·1.25e9 μCi/mol ATP)

The activity of the compounds tested is shown below in Table 2.

| Compound No. | $K_i$ (μmol) |
|---|---|
| 1 | 0.06 |
| 2 | 0.21 |
| 3 | 0.29 |
| 4 | 0.54 |
| 5 | 0.64 |
| 6 | 0.88 |
| 7 | 0.94 |
| 8 | 1.00 |
| 9 | 1.3 |
| 10 | 1.50 |
| 11 | 1.90 |
| 12 | 2.4 |
| 13 | >30 |
| 14 | >30 |

The invention claimed is:

1. A method of inhibiting CAK enzyme from *Candida*, comprising the step of contacting said CAK with a compound of formula (I):

(I)

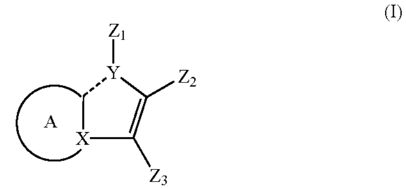

wherein:

X is N;

ring A, taken together with X, is a pyridinyl ring;

Y is =C;

one of $Z^1$ and $Z^3$ is selected from —CN, —$N_3$, acetenyl or cyclopropyl, and the other of $Z^1$ and $Z^3$ is:

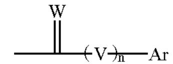

wherein:

n is 0 or 1;

W is O or S;

V is —NH—;

Ar is phenyl or a 5- or 6-membered aromatic heterocyclic ring;

wherein Ar has up to 3 substituents selected from halogen, hydroxyl, nitro, trifluoromethyl, trifluoromethoxy, (C1–C6)-straight or branched alkyl, (C2–C6)-straight or branched alkenyl, O—(C1–C4)-straight or branched alkyl, O—(C2–C4)-straight or branched alkenyl, O-benzyl, O-phenyl, 1,2-methylenedioxy, amino, carboxyl, N—[(C1–C5)-straight or branched alkyl or (C2–C5)-straight or branched alkenyl]carboxamide, N,N-di-[(C1–C5)-straight or branched alkyl or (C2–C5)-straight or branched alkenyl]carboxamide;

$Z_2$ is $N(R^1)_2$, wherein each $R^1$ is independently H, C1–C6 alkyl or C2–C6 alkenyl or alkynyl, wherein a —$CH_2$— in said alkyl, alkenyl or alkynyl may be replaced by —C(O)—, —C(O)—O—, —O—C(O)—, —C(O)—NH—, —NH—C(O)—, —O—, or —S—.

2. The method according to claim 1, wherein $Z_1$ is —CN, —$N_3$, acetenyl or cyclopropyl.

3. The method according to claim 1, wherein $Z_3$ is:

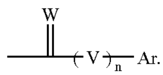

4. The method according to claim 3, wherein W is O, n is 0 and Ar is selected from phenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl or 1,3,5-trithianyl, wherein Ar has up to three substituents independently selected from halogen, hydroxyl, nitro, trifluoromethyl, trifluoromethoxy, (C1–C6)-straight or branched alkyl, (C2–C6)-straight or branched alkenyl, O—(C1–C4)-straight or branched alkyl, O—(C2–C4)-straight or branched alkenyl, O-benzyl, O-phenyl, 1,2-methylenedioxy, amino, carboxyl, N—[(C1–C5)-straight or branched alkyl or (C2–C5)-straight or branched alkenyl] carboxamide, N,N-di-[(C1–C5)-straight or branched alkyl or (C2–C5)-straight or branched alkenyl]carboxamide.

5. The method according to claim 4, wherein Ar is phenyl, 2-furyl, 3-furyl, 2-thienyl, 3-thienyl, 2-pyridyl, 3-pyridyl, 4-pyridyl, pyrrolyl, oxazolyl, thiazolyl or imidazolyl.

6. The method according to claim 5, wherein Ar is phenyl.

7. The method according to ciaim 1, wherein Ar has up to two substituents.

8. The method according to claim 1, wherein Ar has one substituents.

9. A method of inhibiting CAK enzyme from *Candida*, comprising the step of contacting said CAK with a compound of formula (I'):

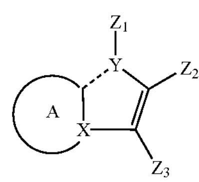

wherein:

X is N;

Y is ═C ring A taken together with X, is a pyridinyl ring, wherein each R is independently H, (C1–C6) straight or branched alkyl, (C2–C6) straight or branched alkenyl or alkynyl;

one of $Z^1$ and $Z^3$ is selected from —CN, —$N_3$, acetenyl or cyclopropyl, and the other of $Z^1$ and $Z^3$ is:

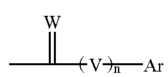

wherein:

n is 0 or 1;

W is O or S;

V is —NH—;

Ar is a 5–10 membered monocyclic or bicyclic aromatic carbocyclic or aromatic heterocyclic ring;

wherein Ar has up to 3 substituents selected from halogen, —OH, —$NO_2$, —$CF_3$, —$OCF_3$, R, —OR, —O-benzyl, —O-phenyl, 1,2-methylenedioxy, —$NR_2$, —COR, —$CO_2R$, —$CON(R)_2$, —$NRCON(R)_2$, —NRCOR, —$NRCO_2R$, —CO—COR, —$CONRN(R)_2$, —$SO_2R$, —SOR, —$SON(R)_2$, —$SO_2N(R)_2$ and —$NRSO_2R$;

$Z^2$ is $NHR^1$;

wherein $R^1$ is H or C1–C6 straight or branched alkyl;

provided that when $Z^1$ is CN, $Z^2$ is —$NH_2$, W is O and n is 0, then Ar is not unsubstituted phenyl.

10. The method according to claim 9, wherein:

W is O; and n is 0.

11. A method of inhibiting CAK enzyme from *Candida*, comprising the step of contacting said CAK with a compound of formula (II):

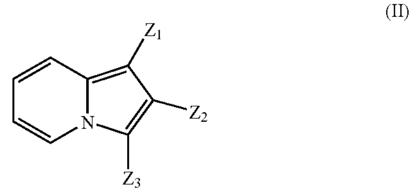

wherein:

$Z_1$ is —CN, —$N_3$, acetenyl or cyclopropyl;

$Z_2$ is —$N(R^1)_2$, wherein each $R^1$ is independently H, C1–C6 alkyl, C2–C6 alkenyl or alkynyl, wherein a —$CH_2$— in said alkyl, alkenyl or alkynyl may be replaced by —C(O)—, —C(O)—O—, —O—C(O)—, —C(O)—NH—, —NH—C(O)—, —O—, or —S—;

$Z_3$ is:

W ‖ —(V)$_n$—Ar wherein n is 0;

W is O;

V is —NH—;

Ar is a 5–10 membered monocyclic or bicyclic aromatic carbocyclic or aromatic heterocyclic ring;

wherein Ar has up to 3 substituents selected from halogen, —OH, —$NO_2$, —$CF_3$, —$OCF_3$, R, —OR, —O-benzyl, —O-phenyl, 1,2-methylenedioxy, —$NR_2$, —COR, —$CO_2R$, —$CON(R)_2$, —$NRCON(R)_2$, —NRCOR, —$NRCO_2R$, —CO—COR, —$CONRN(R)_2$, —$SO_2R$, —SOR, —$SON(R)_2$, —$SO_2N(R)_2$ and —$NRSO_2R$;

wherein each R is independently H, (C1–C6) straight or branched alkyl, (C2–C6) straight or branched alkenyl or alkynyl;

provided that when Y is ═C, $Z^1$ is CN, $Z^2$ is —$NH_2$ and W is O, then: Ar is not unsubstituted phenyl.

12. A method for treating or preventing fungal infection caused by *Candida* in a mammal, comprising the step of administering to said mammal a composition comprising a compound of formula (I), according to claim 1, and a pharmaceutically acceptable carrier.

13. A method of treating a CAK-mediated infection caused by *Candida* in a mammal, comprising the step of administering to said mammal a composition comprising a compound of formula (I), according to claim 1, and a pharmaceutically acceptable carrier.

14. The method according to claim 13, wherein said infection is caused by *Candida albicans, Candida stellatoidea, Candida tropicalis, Candida parapsilosis, Candida krusei, Candida pseudotropicalis, Candida guilliermondii, Candida glabrata, Candida lusianiae*, or *Candida rugosa.*

15. A method of treating or preventing a fungal infection caused by *Candida* in a plant, comprising the step of administering to said plant a composition comprising a compound of formula (I), according to claim 1, and a pharmaceutically acceptable carrier.

16. A method of removing or preventing fungal contamination caused by *Candida* in an inanimate surface, comprising the step of contacting said surface with a composition comprising a compound of formula (I) according to claim 1.

17. A method for treating or preventing fungal infection caused by *Candida* in a mammal, comprising the step of administering to said mammal a composition comprising a compound of formula (II) according to claim 11, and a pharmaceutically acceptable carrier.

18. A method of treating a CAK-mediated infection caused by *Candida* in a mammal, comprising the step of administering to said mammal a composition comprising a compound of formula (II), according to claim 11, and a pharmaceutically acceptable carrier.

19. The method according to claim 17, wherein said infection is caused by *Candida albicans, Candida stellatoidea, Candida tropicalis, Candida parapsilosis, Candida krusei, Candida pseudotropicalis, Candida guilliermondii, Candida glabrata, Candida lusianiae*, or *Candida rugosa.*

20. The method according to claim 18, wherein said infection is caused by *Candida albicans, Candida stellatoidea, Candida tropicalis, Candida parapsilosis, Candida krusei, Candida pseudotropicalis, Candida guilliermondii, Candida glabrata, Candida lusianiae*, or *Candida rugosa.*

21. A method of treating or preventing a fungal infection caused by *Candida* in a plant, comprising the step of administering to said plant a composition comprising a compound of formula (II), according to claim 11, and a pharmaceutically acceptable carrier.

22. A method of removing or preventing fungal contamination caused by *Candida* in an inanimate surface, comprising the step of contacting said surface with a composition comprising a compound of formula (II) according to claim 11.

* * * * *